United States Patent [19]

Maeda et al.

[11] Patent Number: 4,906,569
[45] Date of Patent: Mar. 6, 1990

[54] PROCESS FOR ISOLATING AND RECOVERING ERTHRITOL FROM CULTURE MEDIUM CONTAINING THE SAME

[75] Inventors: Toshihiro Maeda; Isao Nakazawa, both of Zama; Takashi Kombu, Yokohama, all of Japan

[73] Assignees: Mitsubishi Kasei Corporation; Nikken Chemicals Company, Limited, both of Japan

[21] Appl. No.: 304,794

[22] Filed: Jan. 31, 1989

[30] Foreign Application Priority Data

Feb. 2, 1988 [JP] Japan .................................. 63-21347
Jun. 22, 1988 [JP] Japan ................................ 63-152118

[51] Int. Cl.$^4$ ........................ B01D 15/08; C12P 7/18; C12R 1/01
[52] U.S. Cl. .................................... 435/158; 435/822; 435/923; 210/659
[58] Field of Search ....................... 435/158, 923, 822; 210/659

[56] References Cited

U.S. PATENT DOCUMENTS 4,379,751  4/1983  Yoritomi et al. .................... 210/659

FOREIGN PATENT DOCUMENTS 0041549  10/1972  Japan .................................. 435/158
0118889  11/1974  Japan .
0142930   3/1982  Japan .
0106632   7/1982  Japan .

Primary Examiner—Herbert J. Lilling
Attorney, Agent, or Firm—Jordan B. Bierman

[57] ABSTRACT

A process for readily isolating and recovering highly pure erythritol at a high crystallization yield from an erythritol-containing culture medium, which contains erythritol together with various impurities such as salts, coloring materials and polysaccharides, through chromatographic separation with the use of a strongly acidic cation exchange resin. The process of the present invention can be continuously operated, since the lowered separation capability of said cation exchange resin can be readily restored by treating the same with a warm alkali solution.

7 Claims, 1 Drawing Sheet

PROCESS FOR ISOLATING AND RECOVERING ERTHRITOL FROM CULTURE MEDIUM CONTAINING THE SAME

BACKGROUND OF THE INVENTION

1. Field of the Invention

This invention relates to a process for readily isolating and recovering highly pure erythritol at a high crystallization yield from a culture medium of an erythritol-producing bacterium (microorganism), which comprises readily separating and removing various impurities and by-products, for example, various salts, coloring materials and polysaccharides originating from starting raw materials and from additives added to the medium.

2. Prior Art

The term "erythritol" used herein exactly means meso-erythritol which is useful as a sweetener or as an intermediate in the preparation of various drugs or industrial chemicals.

Examples of known erythritol-producing bacteria which produce erythritol through fermentation include those belonging to the genus Aureobasidium producing glycerol as the main by-product (JP-A-61-31091, the term "JP-A" herein used mean unexamined and published Japanese Patent application); Moniliella tomentosa var. pollinis producing glycerol and ribitol which is a sugar alcohol carrying five carbon atoms (JP-A-60-110295~110298), Candida Zeylonoides (ATCC 15585) and Torulopsis famata (ATCC 15586) (JP-A-49-118889); Candida lypolytica (U.S.P. 3,756,917); and those belonging to the genera Trigonopsis and Candida (JP-B-47-41549, the term "JP-B" herein used means examined Japanese patent publication.

A conventional process for isolating and recovering erythritol from a culture medium obtained by culturing one of these erythritol-producing bacteria in an aqueous medium comprises subjecting said culture medium to a pretreatment such as decoloration with the use of activated carbon, desalting and decolorizing the culture medium with ion exchange resins and then concentrating and cooling the same to thereby crystallize the aimed erythritol.

During the culture of an erythritol-producing bacterium, a large amount of inorganic salts such as $KH_2PO_4$, $MgSO_4$, $CaCl_2$, $K_2SO_4$, $CaSO_4$, $FeSO_4$, $MnSO_4$, $ZnSO_4$ or $(NH_4)_2HPO_4$ and nitrogen sources such as $(NH_4)_2SO_4$, urea, $NH_4Cl$ or $NH_4NO_3$ are added to the medium. Further a large amount of nutritional sources such as corn steep liquor, soybean meal, various amino acids, peptone, thiamin or yeast extract are added thereto. When corn steep liquor is added, a particularly remarkable coloration of the culture medium is observed. Therefore the conventional process as described above is disadvantageous, because a large amount of activated carbon and/or ion exchange resins as well as chemicals for regenerating the same are required in order to completely decolorize or desalt the impurities originating from these additives.

In addition, various by-products such as glycerol, ribitol or polysaccharides are formed during the course of the culture in the abovementioned process. When crystalline sucrose or crystalline glucose to be used as a starting raw material is substituted with refined glucose obtained by, for example, enzymatic saccharification of starch, which comprises 93 to 97% of glucose and the residual amount of oligosaccharides such as disaccharides, trisaccharides or higher ones, the oligosaccharides contained in the starting raw material would remain as impurities in the culture medium. These impurities can not be removed by treating the culture medium with activated carbon or decolorizing or desalting the same with the use of ion exchange resins. When the culture medium is concentrated to thereby improve the crystallization yield of the erythritol, the concentration of these impurities is also increased. As a result, the concentrate to be crystallized becomes highly viscous, just like corn syrup, which considerably lowers the crystallization rate of the erythritol. Therefore it is unavoidable to concentrate the culture medium to a limited extent, which significantly lowers the crystallization yield of the aimed erythritol.

Under these circumstances, we have found that the impurities affecting the crystallization of erythritol mainly comprise the following constituents.

(i) Glycerol formed by a side reaction.
(ii) By-products other than glycerol.
(iii) When refined glucose obtained by, for example, enzymatic saccharification of starch is used as a starting raw material, oligosaccharides including disaccharides and higher ones contained in the starting glucose as well as reaction products formed therefrom.
(iv) Polysaccharides comprising glucose as the main constituent and having $\beta$-1,4 bonds.

When the culture medium containing a large amount of the impurities (i), (ii) and (iii) is decolorized/desalted with the use of activated carbon and ion exchange resins in a conventional manner and then crystallized by concentrating, the mother liquor would show a rapid increase in viscosity and thus becomes just like corn syrup before a satisfactory crystallization yield is achieved. As a result, the crystallization rate is considerably lowered and it becomes difficult to separate the precipitated crystals from the mother liquor.

The polysaccharides, i.e., the impurities (iv) have high molecular weights of several thousands to several ten thousands and thus formed at a low concentration, i.e., 30 to 500 ppm. However it is impossible to remove them by conventional methods such as decolorization/desalting with the use of activated carbon or ion exchange resins. Therefore these polysaccharides would be precipitated during the crystallization of erythritol. As a result, the obtained erythritol crystals are contaminated with the polysaccharides. Thus an aqueous solution of the obtained erythritol crystals is turbid, which lowers the qualities.

In order to improve the crystallization yield of erythritol, it is possible to substitute the starting glucose obtained by enzymatic saccharification of starch which contains a large amount of oligosaccharides including disaccharides and higher ones with crystalline glucose or crystalline sucrose to thereby lower the content of the oligosaccharides originating from the starting raw material as well as products formed therefrom, namely the impurities (iii) as defined above. However this method is also unsatisfactory, since the culture medium still contains the impurities (ii), i.e., by-products other than glycerol.

Further there have been proposed processes for separating ethylene glycol from a solution containing the same together with coloring materials and organic acids which comprise subjecting to said solution to chromatography with the use of a cation exchange resin of, for example, a sodium salt type as an separation medium (JP-A-57-106632, 57-142930 and 57-142931). The application of each of these processes; wherein water is used as an eluent, is limited to the separation of ethylene glycol from organic acid salts and coloring materials.

Furthermore there have been shown elusion curves formed by ion exclusion of sodium chloride/glycerol (Gupta, 1971) and sodium chloride/glucose (Singh, 1978) with the use of sodium type cation exchange resin as a separation medium (Prem C. Nigam et al., Studies on Ion-Exclusion Phenomena, Ind. Eng. Chem. Process Des. Dev. 20, 182-188 (1981); Gupta A. K. M, Tech. Thesis, IIT, Kanpur, India (1977); and Singh, D.M., Tech. Thesis, IIT, Kanpur, India (1978).

However these references neither describe nor suggest the process of the present invention which comprises subjecting an erythritol-containing culture medium to chromatography with the use of an alkali metal or ammonium type cation exchange resin as an separation medium to thereby efficiently remove various salts, coloring materials, various oligosaccharides and polysaccharides from said culture medium and thus isolating and recovering highly pure erythritol crystals at a high crystallization yield.

We have further conducted extensive studies to overcome the above problems and consequently succeeded in achieving the object by carrying out chromatography with the use of alkali metal or ammonium type strongly acidic cation exchange resins as separating mediums.

The separation capability of the strongly acidic cation exchange resins to be used in the present invention would be lowered when used repeatedly. However it can be readily restored by washing the cation exchange resins with warm alkali solutions, which enable the prolonged continuous operation of the process of the present invention.

SUMMARY OF THE INVENTION

An object of the present invention is to provide an improved process for isolating and recovering erythritol from an erythritol-containing culture medium. This process comprises efficiently and simultaneously removing various salts, coloring materials, various oligosaccharides and polysaccharides from a supernatant obtained by removing cells from an erythritol-containing culture medium to thereby isolate and recover highly pure erythritol crystals at a high crystallization yield.

The process of the present invention comprises culturing an erythritol-producing bacterium in an aqueous medium under aerobic conditions; removing the cells from the resulting culture medium; passing the obtained supernatant through separation columns packed with alkali metal or ammonium type strongly acidic cation exchange resins; eluting the same with water; collecting fractions containing erythritol as the main component therefrom; and then recovering the aimed erythritol from these fractions.

BRIEF DESCRIPTION OF THE DRAWINGS

FIG. 1 shows relationship among the effluents effusing when the eluate from the separation column of Example 1 was dissolved in eluent water and amounts thereof. In this figure, A represents a relationship between the amount of the effluents and the degree of coloration thereof, while B represents that between the amount of the effluents and the concentration of each constituent.

DETAILED DESCRIPTION OF THE INVENTION

In the isolation/recovery process of the present invention, an erythritol-producing bacterium is cultured in an aqueous medium under aerobic conditions and the cells are removed from the culture medium. Then the supernatant thus obtained is subjected to chromatographic separation with the use of an alkali metal or ammonium type strongly acidic cation exchange resin as a separation medium. It is preferable that hard components of salts are preliminarily removed from the abovementioned supernatant and that said supernatant is then concentrated to a definite concentration.

The removal of the hard components of salts from the supernatant, namely, softening treatment may be commonly carried out by either of these two methods. The first softening method comprises passing said supernatant through a column packed with a strongly acidic sulfonate cation exchange resin of sodium salt type to thereby exchange Ca and/or Mg ions contained in the supernatant with Na ion; then regenerating the cation exchange resin converted to Ca and/or Mg type into the original Na-type by washing the same with an NaCl aqueous solution; and repeatedly using the same. The second softening method comprises passing said supernatant through a column packed with a weakly acidic carboxylate cation exchange resin of Na-type to thereby exchange the hard components therein with Na ion, similar to the first method; regenerating the cation exchange resin converted to Ca and/or Mg type into H-type by washing the same with a strong acid solution such as HCl or $H_2SO_4$; then converting the cation exchange resin into the original Na-type by passing an NaOH aqueous solution therethrough; and repeatedly using the same. The abovementioned supernatant generally contains a large amount of salts, namely, at a total salt concentration of 20 to 300 meq/l. In order to completely remove the hard components from the supernatant having such a high salt concentration as described above, the latter softening method wherein a weakly acidic carboxylate cation exchange resin of Na-type is used is preferable to the first one.

As the strongly acidic cation exchange resins of alkali metal or ammonium type to be used in the process of the present invention as separating mediums, strongly acidic cation exchange resins of divinylbenzene crosslinked polystyrene sulfonate type having a degree of crosslinking of 4 to 10% of alkali metal or $NH_4$ type are preferable. Among these cation exchange resins, those of Na-type are still preferable.

The supernatant as described above, preferably from which the hard components have been preliminarily removed and still preferably which has been concentrated to a concentration of the dissolved materials of 30 to 70% by weight, is fed into a column packed with the abovementioned strongly acidic cation exchange resin of alkali metal or ammonium type, which will be simply called the separating medium hereinafter, at a ratio of 5 to 20% by volume based on the packed volume of the separating medium. Subsequently it is eluted with water and fractions containing erythritol as the main component are collected from the eluate. During this stage, the separation column is maintained at a temperature of 50° to 90° C., preferably 60° to 80° C. When the separation column temperature is excessively low, microorganisms would grow in the separation column, which increases the loss in the pressure of the passing liquid and causes channeling to thereby lower the separation performance. When the separation column temperature is excessively high, on the other hand, disaccharides or higher oligosaccharides contained in the culture medium would be thermally decomposed, which causes serious coloration of the culture medium. When the concentration of the supernatant, which is obtained by removing the hard components, to be fed into the separation column is excessively high, the viscosity of the concentrate is increased while the separation performance of the column is lowered. When this concentration is excessively low, on the other hand, the volume of the supernatant to be fed into the separation column becomes too large and thus the amount of the water employed as the eluent is also increased. Therefore it is preferable that the supernatant to be fed into the separation column has a concentration of the dissolved matters of 30 to 70% by weight, as described above. When the amount of the concentrated supernatant to be fed into the separation column is decreased, the separation performance is increased but the separation capacity per unit volume of the separation medium is lowered. When the amount of the concentrated supernatant is excessively large, on the other hand, the separation performance is lowered. Thus it is preferable that the concentrated supernatant is fed into the separation column at a ratio of 5 to 20% by volume based on the volume of the separation medium, as described above.

The above mentioned culture medium generally contains a large amount of salts including potassium ion and $NH_4$ ion added as nitrogen sources. Although some portion of these ions is substituted with Na ion during the removal process of the hard components, most of them still remain therein and are thus fed into the separation column. As a result, some portion of an Na-type cation exchange resin, which has been packed into the separation column, might be substituted with K or $NH_4$ type after repeatedly carrying out the separation. However this substitution causes no trouble from the viewpoint of separation performance and capability.

The supernatant, which is preferably free from any hard components and adjusted to a definite concentration, is passed through the column followed by water which is used as an eluent. Thus dissolved materials adsorbed by the separating medium are successively eluted. As a result, salts, coloring materials and polysaccharides having large molecular weights are eluted first followed by oligosaccharides including disaccharides and higher ones which are contained in the starting glucose and by-products other than glycerol. Subsequently erythritol and glycerol are eluted. The eluate is divided into two fractions, namely, one obtained before the initiation of the elution of the erythritol and another one obtained thereafter. The former fraction thus obtained contains salts, coloring materials, polysaccharides formed by side-reactions, oligosaccharides including disaccharides and higher ones contained in the starting glucose and other by-products, while the latter one contains erythritol as the main component together with glycerol.

Figure 1A:
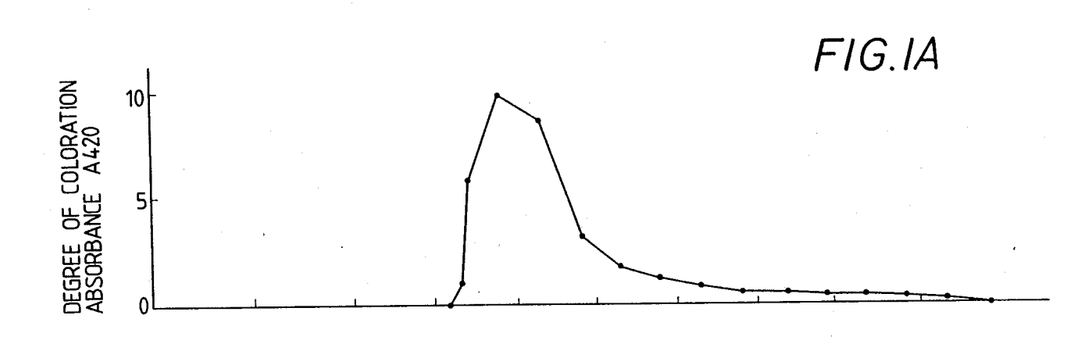
Figure 1B:
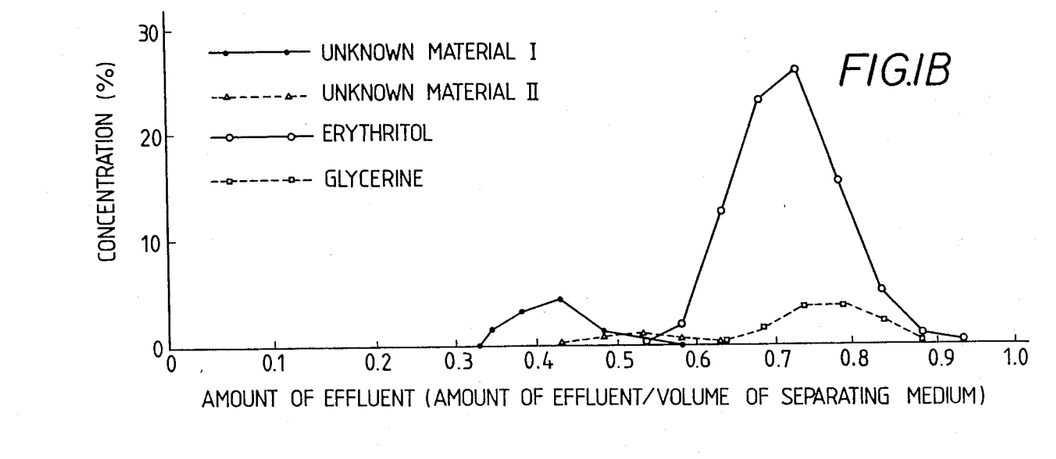

For example, FIG. 1 A shows the relationship between the amount of the eluate eluted with water and the degree of coloration, while FIG. 1 B shows the relationship among the amount of the same eluate, components of the same and concentrations thereof.

FIG. 1 B obviously indicates that salts contained in the culture medium, polysaccharides formed by the erythritol-producing bacterium during the culture and polysaccharides such as dextrin which are contained in starting raw materials added to the culture medium are first eluted as the unknown materials I. Subsequently oligosaccharides including disaccharides and higher ones, which are contained in the starting raw materials, and by-products other than glycerol formed during the culture are eluted as unknown materials II. Then the object erythritol and glycerol, which is a by-product, is eluted. Thus the fraction containing erythritol can be readily separated from that containing other components by dividing the eluate into two fractions at the point when the elution of the erythritol begins.

FIG. 1 A obviously indicates that most of the coloring materials are contained in the former fraction. Thus the erythritol containing fraction contains little coloring materials.

In an embodiment of the isolation/recovery process of the present invention on an industrial scale, the supply of the abovementioned supernatant into a separating medium and the elution of the same with water may be carried out by repeating the supply of the supernatant into a separation column packed with the separating medium and the elution of the same. However the repeated supply and elution may cause a gradual decrease in the separation capability of the separating medium. In order to prevent this decrease, the separating medium, more particularly, an alkali metal or ammonium type strongly acidic cation exchange resin is treated with a warm alkali solution to thereby restore the separation capability thereof and then reused. This is the largest advantage of the present invention.

Examples of the alkali solution include those of alkali metal hydroxides such as sodium hydroxide or potassium hydroxide and hydroxides of alkaline materials such as ammonia. Among these materials, sodium hydroxide is highly preferable.

The treatment of the separating medium of lowered separation capability with the warm alkali solution may be carried out by various methods. It is effected in general by washing the separating medium packed in the column with water, feeding the warm alkali solution thereto and immersing the separating medium in the warm alkali solution for 1 to 10 hours. An alternate method may be effected as follows. Namely, a warm alkali solution is fed into the column through a pump at the top of the separation column to thereby withdraw the liquid within the column. When the run-off of the alkali solution from the bottom of the column is observed, the bottom flow line is converted from a purge line into an alkali solution line to thereby return the alkali solution flow into an alkali solution tank. Thus the warm alkali solution is circulated for 1 to 10 hours. These methods are advantageous from an industrial viewpoint. The warm alkali solution treatment enables to readily remove polysaccharides deposited on the surface of the separating medium through dissolution and to remove proteins similarly deposited thereon through hydrolysis. Thus the separation capability of the separating medium can be readily restored. It is preferable that this treatment is carried out at a temperature of 35° to 100° C., still preferably 50° to 80° C., to thereby facilitate the removal of the deposited matters. It is further preferable to use an aqueous solution of an alkali metal hydroxide having a concentration of 0.1 to 15% by weight, still preferably 0.5 to 10% by weight.

As the alkali, one having the same ion type as that of the separating medium, namely, an alkali metal or ammonium type strongly acidic cation exchange resin is preferably selected, since it causes no change in the ion type of the separating medium. In this case, therefore, the treated separating medium may be reused in the separation procedure after simply washing the same with water.

It has been believed that the separation capability of a strongly acidic cation exchange resin on the surface of which organic matters are deposited can be restored only to a limited extent, even though it is washed with an acid or alkali solution (for example, JA-A-57-59641, p, 3, l. 13 in left/upper col. to l. 2 in right/upper col.). In contrast thereto, the process of the present invention exerts an unexpected effect that the lowered separation capability of a strongly acidic cation exchange resin can be readily restored simply by treating the same with a warm alkali solution.

The fraction containing erythritol as the main component thus obtained is sufficiently free from coloring materials and salts. Thus it may be concentrated as such to thereby readily precipitate highly pure erythritol crystals at a high crystallization yield. That is to say, the abovementioned generally contains dissolved erythritol at a concentration as low as 3 to 30% weight together with glycerol which is a by-product. Highly pure erythritol can be crystallized from this fraction by concentrating the same. For example, this fraction is concentrated to give a concentration of the dissolved matters of 30 to 85% by weight and crystal seeds of erythritol are added thereto. Then the aimed crystals are precipitated under slowly cooling (crystallization). Alternately the abovementioned fraction is concentrated under reduced pressure at a constant temperature ranging from 30° to 80° C. to thereby precipitate erythritol crystals. Thus highly pure erythritol crystals can be obtained at a high crystallization yield.

When it is required to obtain particularly pure erythritol crystals, the fraction containing erythritol as the main component which is obtained above is decolorized with activated carbon and then completely desalted in a conventional manner with the use of a column packed with a cation exchange resin, that packed with an anion exchange resin and that packed with a cation exchange resin and anion exchange resin mixture in sequence. Then the fraction is concentrated and crystallized in the same manner as described above to precipitate erythritol crystals in high purity.

After precipitating the erythritol crystals, the mother liquor still contains glycerol which is a by-product. This glycerol may be readily and separately recovered.

Accordingly the process of the present invention enables to divide an eluate of a supernatant of a culture medium, which contains various impurities such as salts added to the medium, oligosaccharides including disaccharides and higher ones contained in the starting glucose and various by-products other than glycerol formed by side reactions, into two fractions, namely, one which is eluted at an early stage and contains most of these impurities as well as coloring materials and another one which is eluted at the latter stage and contains erythritol as the main component. Thus the latter fraction contains erythritol as the main component and an extremely small amount of impurities. Accordingly highly pure erythritol can be crystallized at a high crystallization yield from the latter fraction which contains an extremely small amount of sugars and sugar alcohols to be purged.

The process of the present invention is further advantageous in that the separation capability of a separating medium which is lowered by repeated elution of the supernatant can be readily restored by a simple treatment, which enables to effectively use the separating medium for a prolonged period of time.

The above description relates to a batchwise separation process. To further illustrate the chromatographic separation procedure, the Examples which are disclosed hereinafter will be given.

Example 1 shows the most simple batchwise separation process wherein a definite amount of a concentrated supernatant from which cells have been removed is fed into the top of a separation column and the eluate thus obtained from the bottom of the column is divided into a fraction containing salts, polysaccharides and by-products other than glycerol and another one containing erythritol as the main component. Example 2 shows a process wherein a small amount of the eluent is required compared with the process of Example 1. In this process, a definite amount of supernatant from which cells have been removed is fed into the top of a separation column and then the eluate containing erythritol as the main component is collected from the bottom of the column (the first step). Subsequently the liquid contained in the column is circulated from the bottom to the top to thereby chromatographically separate the erythritol from various impurities including salts, coloring materials, polysaccharides and oligosaccharides within the column. When the head of the intracolumn separation peak of the concentration of the unknown materials I consisting of salts, coloring materials and polysaccharides (FIG. 1) reaches the bottom of the column, the circulation from the bottom to the top is ceased (the second step). Then the eluent is fed into the top of the column and the unknown materials including salts, coloring materials, polysaccharides and oligosaccharides are purged (removed) from the bottom of the column. When the head of the intracolumn separation peak of the concentration of erythritol reaches the bottom of the column, the purge from the bottom of the column is ceased (the third step). Subsequently the eluate is fed into the top of the column and a fraction containing erythritol as the main component is collected (the fourth step). Thus erythritol can be efficiently separated from impurities such as salts, coloring materials, polysaccharides and oligosaccharides by successively repeating these four steps. In the first step, a fraction containing erythritol is drawn from the bottom of the column. At the completion of the first step, it is preferable, in order to achieve a high yield of the erythritol, that the amount of the erythritol remaining at the bottom of the column and in the packed separating medium is as small as possible. When a large amount of erythritol remains at the bottom of the column, the head of the intracolumn separation peak of the concentration of the unknown materials I (FIG. 1) overlap with the tailing of that of the erythritol at the second step. As a result, the tailing of the intracolumn separation peak of the erythritol remains at the bottom of the column and the erythritol is purged together with the unknown materials I and II at the third step, even if the second step is appropriately terminated and the circulation is ceased when the head of the intracolumn separation peak of the concentration of the unknown material I reaches the bottom of the column. Thus the yield of the erythritol is significantly lowered thereby. When the termination of the second step is somewhat retarded and the tailing of the intracolumn separation peak of the concentration of the erythritol is shifted from the bottom of the column to the top of the same to thereby avoid any decrease in the yield of the erythritol, on the contrary, some portion of the head of the intracolumn separation peak of the concentration of the unknown material I would shift into the top of the column. As a result, the erythritol fraction is contaminated with these unknown materials at the fourth and first steps, which makes the subsequent desalting, decoloration and crystallization highly difficult. In order to avoid these troubles, it is highly important to avoid the overlap of the head of the intracolumn separation peak of the concentration of the unknown materials I and the tailing of the intracolumn separation peak of the erythritol concentration and to control the amount of the eluent to be fed at the fourth step and that of the concentrated supernatant to be fed at the first step in such a manner as to make the composition of the liquid in the packed layer at the top of the column substantially water.

Example 3 shows a process obtained by further improving the procedure described in Example 2. In the early stage in the fourth step of the process of Example 2, the tailing of the intracolumn separation peak of the unknown material II containing oligosaccharides is eluated together with erythritol, as shown in FIG. 1, it is impossible to remove these oligosaccharides at a high ratio. This problem is solved by the process of Example 3. In this process, a definite amount of concentrated supernatant from which cells have been removed are fed into the top of the column and a fraction containing erythritol as the main component is collected from the bottom of the column (the first step). Then the liquid in the column is circulated from the bottom of the column to the top of the same to thereby chromatographically separate the erythritol from various impurities such as salts, coloring materials, polysaccharides and oligosaccharides within the column. When the head of the intracolumn separation peak of the unknown materials I in FIG. 1 consisting of salts, coloring materials and polysaccharides reaches the bottom of the column, the circulation from the bottom to the top is ceased (the second step). Subsequently the eluent water is fed into the packing layer, which is located above the packing part where the tailing of the intracolumn separation peak of the erythritol concentration is present and substantially comprises water, and unknown materials including salts, coloring materials, polysaccharides and oligosaccharides are purged from the bottom of the column. When the head of the intracolumn separation peak of the erythritol concentration reaches the bottom of the column, the purge is ceased (the third step). At the completion of the third step, a mixture of the tailing of the intracolumn separation peak of the concentration of the unknown material II (FIG. 1) and the head of the intracolumn separation peak of the erythritol concentration present below the packing part is shifted to the top of the column while the tailing of the intracolumn separation peak of the concentration of the unknown materials II is completely shifted from the bottom of the column to the top of the same. Then the circulation from the bottom of the column to the top of the same is ceased (the fourth step). Subsequently eluent water is fed into the packing part, which is located above the tailing of the intracolumn separation peak of the erythritol concentration and below the head of the intracolumn separation peak of the concentration of the unknown materials II shifted to the top of the column at the fourth step and substantially comprises water, to thereby collect a fraction containing erythritol as the main component from the bottom of the column (the fifth step). After successively repeating these five steps, both of the purge ratio of the impurities and the yield of the erythritol can be significantly elevated.

As described in the illustration of the process of Example 2, it is required, in order to secure these excellent separation effects, to adjust the amounts of the concentrated supernatant, from which cells have been removed, to be fed at the first step and the amount of the eluent water to be fed at the fifth step in such manner as to make the composition of the part between the head of the intracolumn separation peak of the concentration of the impurities and the tailing of the intracolumn separation peak of the erythritol concentration substantially water at the termination of the second step, i.e., the circulation of liquid in the column and the fourth step. Without these adjustments, the erythritol yield at the chromatographic separation would be lowered, the load at the purification, desalting or decolorization would be increased and/or the erythritol product would be contaminated with polysaccharides, which makes the purification significantly difficult.

Sanmatsu Kogyo Co. Ltd. has already proposed a chromatographic separation process comprising five steps similar to the one of the present invention (JP-A-53-149870). However the Sanmatsu Kogyo's process aims at elevating the efficiency of a separating medium and lowering the required amount of an eluent. It comprises (1) circulating the head (lower concentration) of the elution separation peak of components never controlled by an adsorbent (A) and the tailing (lower concentration) of the elution separation peak of components controlled by the adsrobent (B); (2) locating the feeding site for an eluent at such a position at which the composition of the liquid in the column is the minimum or at the same level as the eluent; and (3) locating the feeding site for the materials at such a position at which the concentration distribution of the liquid in the column is equal to the mixing ratio of the components (A) and (B) in the materials. Thus it is possible to efficiently carry out the isolation without changing the concentration distribution within the column. This process proposed by Sanmatsu Kogyo is applied to the separation of erythritol. Namely, the component (A) controlled by the separating medium, which comprises salts, coloring materials and polysaccharides contained in the erythritol culture medium, at a lower concentration of the head of its intracolumn separation peak is not eluted but circulated within the column. Then it is difficult to completely separate the ion exchange resin from these impurities and the obtained erythritol crystals are contaminated with polysaccharides. In order to avoid these undesirable results, we have conducted extensive studies and consequently found that the following factors are highly important in readily separating and purifying an erythritol fraction, namely, (i) the circulation at the second step is ceased when the head of the separation peak of the salts, coloring materials and polysaccharides reaches the bottom of the column and then these materials are purged at the third step; and (ii) a packing part which substantially comprises water is present at the upper part of the column at the completion of the circulation at the fourth step and thus the aimed erythritol is clearly separated from impurities thereby, thus completing the present invention.

In the above description, it seems that the procedures of Examples 2 and 3 would be conducted each by using a single separation column. However it is possible to successively bind several columns in series with each other, namely, binding the bottom of a column to the top of the next one with a pipe, depending on, for example, the flow rate in a column, pressure loss through a packed bed, the strength of the separating mediums and the location of liquid distribution tubes. Thus substantially the same result as that obtained by using a single separation column can be achieved. As described above, the above procedures are not limited to the use of a single separation column.

Thus the separation procedures in the processes of Examples 1 to 3 have been described in detail. From the viewpoint of purification effect, a definite amount of a concentrated supernatant may be fed into a separating medium followed by an eluent water to thereby separate the former into a fraction containing salts, polysaccharides and by-products other than glycerol and another one containing erythritol. Any separation procedure may be selected therefor so long as alkali metal or ammonium type strongly acidic cation exchange resins are employed. That is to say, the separation procedure is not limited to those which will be described in the following Examples. For example, a batchwise process proposed by Colonial Sugar Inc. (JP-B-45-24807), another batchwise one proposed by Mitsubishi Chemical Industries, Ltd. (JP-A-55-61903) and a continuous process proposed by U.O.P. Co., USA (U.S.P. 2,985,589) with the use of a pseudo-moving bed may be employed therefor.

As described above, the isolation and recovery process of the present invention enables to readily isolate and recover highly pure erythritol crystals from an erythritol-containing culture medium at a high crystallization yield. The process of the present invention further enables to readily restore the lowered separation capability of strongly acidic cation exchange resins and to reuse the same. Thus erythritol can be advantageously isolated and recovered by continuously using the same strongly acidic cation exchange resins for a prolonged period of time.

To further illustrate the present invention, and not by way of limitation, the following Examples will be given, wherein all parts and percentages are by weight, unless otherwise noted.

EXAMPLE 1

A medium containing 300 g/l, in terms of glucose, of anhydrous crystalline glucose and 6.7 g/l of yeast extract was inoculated with Aureobasidium SN-G42 strain. Then the strain was cultured therein at 30° C. for 72 hours under shaking. 1.5 l of the seed culture thus obtained was added to 25 l of a medium (initial pH value: 4.2) containing 340 g/l of anhydrous glucose and 55 g/l of corn steep liquor and cultured therein at an aeration rate of 25 l/min, at a temperature of 35° C. and under 0.5 kg/cm² G with stirring at 600 rpm for 93 hours. When it was confirmed that the glucose was completely consumed, the culture was ceased and the culture medium was immediately pasteurized by heating. Then it was centrifuged to thereby remove the cells. The supernatant thus obtained contained 187 g/l of erythritol and 25 g/l of glycerol.

19.9 l of this supernatant was passed through a column packed with a carboxylate weakly acidic cation exchange resin of Na type (Diaion WK-20 mfd. by Mitsubishi Kasei Corporation) to thereby substitute the hardness components therein such as Ca and Mg with Na ion. Then it was concentrated until the concentration of the dissolved matters reached 45%.

A separation column (2.8 cm (i.d.) ×200 cm (h)) was packed with 1.24 l of a divinylbenzene crosslinked polystyrene sulfonate resin of Na type (Diaion UBK-530 mfd. by Mitsubishi Kasei Corporation) and maintained at 75° C. 0.124 l of the abovementioned 45% concentrate (75° C.) was fed into the top of the column at a rate of 0.46 l/hr and then water was fed into the top at the same rate. FIG. 1 shows the result of the analysis on the eluate thus obtained from the bottom of the column.

The unknown materials I as shown in FIG. 1 B mainly comprised salts, coloring materials and polysaccharides comprising glucose as the main constituent and carrying $\beta$-1,4 bonds. As shown in FIG. 1, these unknown materials were contained in the fraction eluted at an early stage. The unknown materials II which were subsequently eluted mainly comprised by-products other than glycerol, oligosaccharides including disaccharides and higher ones and reaction products obtained therefrom. These materials were also contained in a fraction eluted at relatively early stage. In this Example, crystalline glucose was used as the starting glucose. Therefore the unknown materials II contained no oligosaccharides such as disaccharides and higher ones nor reaction products obtained therefrom each originating from the starting glucose. Thus the unknown materials II mainly consisted of by-products other than glycerol. Then the aimed erythritol and glycerol were eluted in the final fraction.

As shown in FIG. 1 A, most of the coloring materials were contained in the fractions eluted at early stage.

When this eluate was divided into two fractions obtained before and after the point when the bed volume of the eluate reached 0.54, the former fraction contained most of the coloring materials and nearly all of the unknown materials I and II, while the latter one contained nearly all of the erythritol and glycerol (FIG. 1). Thus the latter fraction contained erythritol as the main component and was almost free from coloring materials, salts nor polysaccharides. In other words, a fraction containing erythritol and glycerol but free from impurities can be readily obtained from the supernatant thereby.

The amount of the former fraction, i.e., the one obtained before the eluate bed volume reached 0.54 was 0.67 l while that of the latter obtained thereafter was 0.47 l.

Then the above procedure was repeated 70 times. Thus 33 l of the latter fractions were obtained in total. These fractions contained 106 g/l of erythritol, 14.2 g/l of glycerol and 0.98 g/l of the unknown materials II. 66 g of powdery activated carbon was added thereto and the resulting mixture was stirred for 30 minutes. After filtering off the activated carbon, the filtrate was successively passed through a column packed with a strongly acidic cation exchange resin of H type (Diaion SK1B mfd. by Mitsubishi Kasei Corporation), that packed with a weakly basic anion exchange resin of OH type (Diaion WA30 mfd. by Mitsubishi Kasei Corporation) and that packed with a mixture of said strongly acidic cation exchange resin of H type and a strongly basic anion exchange resin (Diaion PA408 mfd. by Mitsubishi Kasei Corporation) to thereby further desalt and decolorize the same. Then it was concentrated under reduced pressure at 80° C. to give a concentration of the dissolved matters of 53%.

Subsequently the concentrate at 80° C. was slowly cooled to 15° C. within two hours and maintained at this temperature for additional two hours to thereby promote the growth of crystals. The crystal thus formed were filtered and the resulting moist crystals were washed with water at 15° C. 0.6 times as much as the same. Thus 1.66 kg of erythritol crystals having a purity of 100% were obtained. In this case, the crystallization yield based on the erythritol contained in the 53% by weight concentrate was 47.5%. When these crystals were dissolved in water, the obtained solution (10%) showed no turbidity.

EXAMPLE 2

Refined glucose comprising 96.8% of pure glucose and the residual 3.2% of oligosaccharides including disaccharides and higher ones was employed as the starting glucose. A medium (initial pH value: 4.2) containing 400 g/l, in terms of pure glucose, of this purified glucose and 67 g/l of corn steep liquor was inoculated with 1.5 l of the same seed culture as the one used in Example 1. Then it was cultured therein at a temperature of 35° C., an aeration rate of 13 l/min and under 0.5 kg/cm$^2$ with stirring at 600 rpm. After carrying out the culture for 95 hours, the glucose was completely consumed. Then the culture was immediately ceased and the culture medium was pasteurized by heating. Then the cells were removed therefrom. The supernatant thus obtained (approximately 19.9 l) contained 213 g/l of erythritol, 17.5 g/l of glycerol, 18 g/l of unknown materials I and 16 g/l of unknown materials II.

This supernatant was softened by passing through a column packed with Diaion WK-20 of Na type (mfd. by Mitsubishi Kasei Corporation) and then concentrated to give a concentration of the dissolved matters of 45% by weight. Thus approximately 10.2 l of a concentrate was obtained.

The resulting concentrate and water were passed through a column (2.8 cm (i.d.) ×100 cm (h)) packed with 0.62 l of Diaion UBK-530 of Na type (mfd. by Mitsubishi Kasei Corporation) each at 75° C. and at a constant rate of 0.496 l/hr in the following four steps.

First Step 70 ml of the abovementioned concentrate (45%) was fed into the top of the column and 70 ml of an eluate was collected from the bottom of the column. This eluate, which was obtained by shifting the liquid present in the column in the previous fourth step toward the bottom of the column, contained erythritol as the main component.

Second step 130 ml of the liquid in the column was circulated from the bottom of the column to the top of the same for 15.7 minutes with the use of a pump.

Third step 143 ml of water was fed into the top of the column and 143 ml of an eluate was collected from the bottom of the same. This eluate, which contained various salts, coloring materials and the unknown materials II, was purged as described above.

Fourth step 180 ml of water was fed into the top of the column and 180 ml of an eluate was collected from the bottom of the same. This eluate, which contained erythritol as the main component, was combined with the one obtained in the first step.

After the completion of the fourth step, the first step was initiated again. Thus this cycle consisting of these four steps was repeated until the abovementioned concentrated supernatant (10.2 l) was lost. Thus 36.3 l of a fraction containing erythritol as the main component was obtained.

The analysis of this fraction indicated that it contained 116 g/l of erythritol, 9.6 g/l of glycerol and 2.6 g/l of the unknown materials II; that the desalting ratio thereof was 95% while the decolorization degree thereof was 87%; and that the yield of erythritol was 99.9% while the purge ratio of the unknown material II was 70%. The degree of coloration of this fraction, which was determined from $A_{420}$ by using a 1 cm cell (the same will apply hereinafter), was 0.32 and the electric conductivity thereof was 167 µS/cm.

Then the fraction containing erythritol as the main component (36.3 l) thus obtained was decolorized by adding 0.1% by weight of powdery activated carbon thereto. Thus the degree of coloration was lowered to 0.16. Further the fraction was successively passed through a column packed with a strongly acidic cation exchange resin of H type (Diaion SK1B mfd. by Mitsubishi Kasei Corporation), that packed with a weakly basic anion exchange resin of OH type (Diaion WA30 mfd. by Mitsubishi Kasei Corporation) and that packed with a mixture of said resin of H type and a strongly basic anion exchange resin of OH type (Diaion PA408 mfd. by Mitsubishi Kasei Corporation) to thereby desalt and decolorize the same in a conventional manner. Then it was concentrated under reduced pressure at 80° C. to thereby give a solid content of 61%.

Subsequently the resulting concentrate at 80° C. was slowly cooled to 15° C. within two hours and maintained at this temperature for additional two hours to thereby promote the growth of crystals. The crystals thus formed were filtered and the obtained moist crystals were washed with water at 15° C. 0.6 times as much as the same. After drying, 2.40 kg of erythritol crystals of a purity of 100% were obtained. The crystallization yield of erythritol based on the concentrate (61%) was 57%. When these crystals were dissolved in water, the obtained solution (10% by weight) showed no turbidity.

EXAMPLE 3

Approximately 19.9 l of a pasteurized culture supernatant obtained in the same manner as the one described in Example 2 (composition: 213 g/l of erythritol, 17.5 g/l of glycerol, 18 g/l of the unknown materials I and 16 g/l of the unknown materials II) was softened by passing through a column packed with Diaion WK-20 of Na type (mfd. by Mitsubishi Kasei Corporation) and concentrated under reduced pressure at 80° C. to thereby give a concentration of the dissolved matters of 50.9%. Thus approximately 8.9 l of the concentrate was obtained.

The resulting concentrate and water were passed through a column (2.8 cm (i.d.) ×200 cm (h)) packed with 1.24 l of Diaion UBK-530 of Na type (mfd. by Mitsubishi Kasei Corporation) each at 75° C. and at a constant rate of 0.816 l/hr in the following five steps.

First step 105 ml of the abovementioned concentrate (50.9%) was fed into the top of the column and 105 ml of an eluate was collected from the bottom of the column. This eluate, which was obtained by shifting the liquid present in the column in the previous fifth step toward the bottom of the column, contained erythritol as the main component.

Second step 292 ml of the liquid in the column was circulated from the bottom of the column to the top of the same for 21.5 minutes with the use of a pump. At the completion of the second step, the column top liquid substantially comprised water.

Third step 260 ml of water was fed into the top of the column and 260 ml of a eluate was collected from the bottom of the same. This eluate, which contained various salts, coloring materials and the unknown materials II, was purged as described above.

Fourth step

The liquid present in the column was circulated from the bottom of the column to the top of the same for 6.4 minutes (87 ml). At the completion of the third step, the liquid containing the unknown materials II and erythritol present in the bottom of the column was transported to the top of the column in this fourth step.

Fifth step

The eluent water was fed into a site 50 cm below the top of the column, where the inner liquid substantially comprised water. Then 292 ml of the eluate was collected from the bottom of the column. This eluate, which contained erythritol as the main component, was combined with the eluate obtained in the first step.

After the completion of the fifth step, the first step was initiated again. Thus this cycle consisting of these five steps was repeated until the abovementioned concentrated supernatant (approximately 8.9 l) was lost. Thus 33.6 l of a fraction containing erythritol as the main component was obtained.

The analysis of this fraction indicated that it contained 126 g/l of erythritol, 10.4 g/l of glycerol and 0.1 g/l of the unknown materials; that the desalting ratio thereof was 95.6%; and that the yield of erythritol was 99.4% while the purge ratio of the unknown material II was 99%. The degree of coloration of this fraction, which was determined from A420 by using a 1 cm cell, was 0.32 and the electric conductivity thereof was 195 $\mu$s/cm.

Then the fraction containing erythritol as the main component (33.6 l) thus obtained was decolorized by adding 0.1% by weight of powdery activated carbon thereto. Thus the degree of coloration was lowered to 0.15. Further the fraction was successively passed through a column packed with a strongly acidic cation exchange resin of H type (Diaion SK1B mfd. by Mitsubishi Kasei Corporation), that packed with a weakly basic anion exchange resin of OH type (Diaion WA30 mfd. by Mitsubishi Kasei Corporation) and that packed with a mixture of said resin of H type and a strongly basic anion exchange resin of OH type (Diaion PA408 mfd. by Mitsubishi Kasei Corporation) to thereby desalt and decolorize the same in a conventional manner.

Then it was concentrated under reduced pressure at 80° C. to thereby give a solid content of 64%.

Subsequently the resulting concentrate at 80° C. was slowly cooled to 15° C. within two hours and maintained at this temperature for additional two hours to thereby promote the growth of crystals. The crystals thus formed were filtered and the obtained moist crystals were washed with water at 15° C. 0.6 times as much as the same. After drying, 2.50 kg of erythritol crystals of a purity of 100% were obtained. The crystallization yield of erythritol based on the concentrate (64% by weight) was 59%. When these crystals were dissolved in water, the obtained solution (10%) showed no turbidity.

EXAMPLE 4

Refined glucose comprising 96.8% of pure glucose and the residual 3.2% of oligosaccharides including disaccharides and higher ones was employed as the starting glucose. A medium containing 300 g/l, in terms of pure glucose, of this purified glucose and 6.7 g/l of yeast extract was inoculated with Aureobasidium SN-G42 strain which was then cultured therein at 30° C. for 72 hours under shaking. 1.5 l of the seed culture thus obtained was added to 25 l of a medium (initial pH value: 4.2) containing 400 g/l, in terms of pure glucose, of the abovementioned starting glucose and 67 g/l of corn steep liquor and cultured therein at 35° C. and at an aeration rate of 13 l/min under 0.5 kg/cm$^2$ with stirring at 600 rpm. After carrying out the culture for 95 hours, the glucose was completely consumed. Then the culture was immediately ceased and the culture medium was pasteurized by heating. Then the cells were removed therefrom by centrifuging. The supernatant thus obtained (approximately 19.9 l) contained 213 g/l of erythritol, 17.5 g/l of glycerol, 18 g/l of unknown materials I and 16 g/l of unknown materials II.

This supernatant was softened by passing through a column packed with Diaion WK-20 of Na type (mfd. by Mitsubishi Kasei Corporation) and then concentrated to give a concentration of the dissolved matters of 45%. Thus approximately 10.2 l of a concentrate was obtained.

The resulting concentrate and water were passed through a column (2.8 cm (i.d.) $\times$ 100 cm (h)) packed with 0.62 l of Diaion UBK-530 of Na type (mfd. by Mitsubishi Kasei Corporation) each at 75° C. and at a constant rate of 0.496 l/hr in the following four steps.

First step 70 ml of the abovementioned concentrate (45%) was fed into the top of the column and 70 ml of an eluate was collected from the bottom of the column. This eluate, which was obtained by shifting the liquid present in the column in the previous fourth step toward the bottom of the column, contained erythritol as the main component.

Second step 130 ml of the liquid in the column was circulated from the bottom of the column to the top of the same for 15.7 minutes with the use of a pump.

Third step 143 ml of water was fed into the top of the column and 143 ml of an eluate was collected from the bottom of the same. This eluate, which contained various salts, coloring materials and the unknown materials II, was purged as described above.

Fourth step 180 ml of water was fed into the top of the column and 180 ml of an eluate was collected from the bottom of the same. This eluate, which contained erythritol as the main component, was combined with the one obtained in the first step.

After the completion of the fourth step, the first step was initiated again. Thus this cycle consisting of these four steps was repeated to thereby collect a fraction containing erythritol as the main component. The analysis of this fraction indicated that it contained 116 g/l of erythritol, 9.6 g/l of glycerol and 2.6 g/l of the unknown materials II; that the desalting ratio thereof was 95% while the decolorization degree thereof was 87%; and that the yield of erythritol was 99.9% while the purge ratio of the unknown material II was 70%.

The above cycle consisting of these four steps was repeated 22.8 times per day for 95 days. Then the same culture, softening and concentration as those described above were conducted. The resulting culture medium was subjected to chromatographic separation. As a result, the erythritol fraction obtained on the 95th day contained 115 g/l of erythritol, 9.6 g/l of glycerol and 6.1 g/l of the unknown materials II. The desalting ratio of the fraction was 92% while the decolorization ratio thereof was 85%. The yield of erythritol was 99.0% and the purge ratio of the unknown materials II was 30%. These data were compared with the above ones of the erythritol fraction obtained by using a fresh separating agent. As a result, no significant difference was observed in the separation capability including desalting ratio, decoloration ratio and erythritol concentration, though the purge ratio of the unknown materials II in the former case was lowered to 30%.

Since this decrease in the purge ratio of the unknown materials II would lower the yield of highly pure erythritol at the subsequent crystallization step, the separating medium of the lowered separation capability was treated in the following manner. Namely, the separating medium, whose separation capability was lowered by repeatedly using the same for 95 days, was washed with water at 75° C. Then an aqueous solution of 4% by weight of sodium hydroxide at 75° C. was fed into the top of the separation column. When the elution of the sodium hydroxide from the bottom of the column was initiated, the flow line was changed to thereby return the eluate into a tank of the aqueous solution of sodium hydroxide of the temperature and concentration as defined above. Thus the abovementioned aqueous solution of sodium hydroxide was circulated at a rate of 2 l/hr for three hours. Subsequently the inside of the separation column was washed with water until there remained no alkaline materials. Then a concentrated supernatant obtained by softening and concentrating the same culture medium as the one used above was subjected to the chromatographic separation comprising the same four steps. The analytical data, namely, desalting ratio, decolorization ratio, erythritol yield and purge ratio of the unknown materials II of the fraction containing erythritol as the main component thus obtained were compared with those obtained by using the fresh separating agent and those obtained by using the separating agent repeatedly used for 95 days. Table 1 shows the results. Table 1 obviously indicates that the separation capability of the separating agent lowered by the repeated use was restored almost to the same level as that of the fresh one by treating the same with the aqueous solution of sodium hydroxide.

TABLE 1

| Separating agent | Fresh | Repeatedly used for 95 days | Used and then treated with alkali solution |
|---|---|---|---|
| Desalting ratio (%) | 95 | 92 | 94 |
| Decolorization ratio (%) | 87 | 85 | 88 |
| Erythritol yield (%) | 99.9 | 99.0 | 99.6 |
| Purge ratio of unknown materials II (%) | 70 | 30 | 68 |

COMPARATIVE EXAMPLE 1

The culture supernatant obtained in Example 2 (coloration: 6.2, electric conductivity: 7.0 ms/cm) was decolorized by adding 5% of powdery activated carbon thereto. However the coloration degree was lowered only to 0.35. The decolorized supernatant was desalted by using the same ion exchange resins as those used in Example 2 in a conventional manner. As a result, 20 times as much as the ion exchange resins were required, compared with the case of Example 2.

The decolorized and desalted supernatant was concentrated under reduced pressure at 80° C. to thereby give a solid content of 50%. Then it was subjected to cooling, crystallization, separation of crystals, washing with water and drying, each in the same manner as the one described in Example 2, to thereby give 1.80 kg of crystals of a purity of 100%. In this case, the crystallization yield of erythritol based on the concentrate of 50% by weight was 43.8%.

In order to elevate the crystallization yield of erythritol in the product, the solid content at the concentration under reduced pressure at 80° C. was increased to 60% by weight. Then the purity of the erythritol crystals was lowered to 99.8%. Both of the crystals obtained from the concentrates of 50% and 60% showed turbidity when dissolved in water at a concentration of 10%.

While the invention has been described in detail and with reference to specific examples thereof, it will be apparent to one skilled in the art that various changes and modifications can be made therein without departing from the spirit and scope thereof.

What is claimed is:

1. A process for isolating and recovering erythritol from an erythritol-containing culture medium, which comprises culturing an erythritol-producing bacterium in an aqueous medium under aerobic conditions; removing the cells from the culture medium; passing the supernatant thus obtained through a separation column packed with an alkali metal or ammonium type strongly acidic cation exchange resin; eluting the same with water; collecting a fraction containing erythritol as the main component from the resulting eluate; and recovering the object erythritol from said fraction.

2. A process for isolating and recovering erythritol as set forth in claim 1, wherein a fraction mainly containing erythritol and glycerol is collected from said eluate and then the object erythritol is recovered from said fraction through crystallization.

3. A process for isolating and recovering erythritol as set froth in claim 1, wherein hardness components contained in said supernatant are removed by using an alkali metal type cation exchange resin before passing said supernatant through the separation column.

4. A process for isolating and recovering erythritol as set forth in claims 1, wherein said strongly acidic cation exchange resin is one of Na type.

5. A process for isolating and recovering erythritol as set forth in claim 1, wherein the separation capability of said strongly acidic cation exchange resin, which is lowered by repeating the elution of said supernatant with water, is restored by treating the same with a warm alkali solution at 35° C. to 100° C. and then said cation exchange resin is reused in the separation.

6. A process for isolating and recovering erythritol as set forth in claim 1, wherein the process comprises four steps:
the first step in which said supernatant is fed into the top of said column and an eluate containing erythritol as the main component is collected from the bottom of the same;
the second step in which the liquid in the column is circulated from the bottom to the top;
the third step in which water is fed into the top of the column and an eluate from the bottom thereof is purged; and
the fourth step in which water is fed into the top of the column and an eluate containing erythritol as the main component is collected from the bottom.

7. A process for isolating and recovering erythritol as set forth in claim 1, wherein the process comprises five steps:
the first step in which said supernatant is fed into the top of the column and an eluate containing erythritol as the main component is collected from the bottom;
the second step in which the liquid in the column is circulated from the bottom to the top;
the third step in which water is fed into the upper part (or the top) of the column where the composition of the mixture in the column is substantially water and an eluate from the bottom is purged;
the fourth step in which the liquid in the column is circulated again from the bottom to the top; and
fifth step in which water is fed into the upper part of the column where the mixture concentration in the column is substantially the same as that of water and an eluate containing erythritol as the main component is collected from the bottom.

* * * * *